US00PP09809P

United States Patent [19]

VandenBerg

[11] Patent Number: Plant 9,809

[45] Date of Patent: Feb. 25, 1997

[54] CHRYSANTHEMUM PLANT NAMED 'FELICIA'

[75] Inventor: Cornelis P. VandenBerg, Salinas, Calif.

[73] Assignee: Yoder Brothers, Inc., Barberton, Ohio

[21] Appl. No.: 609,493

[22] Filed: Mar. 1, 1996

[51] Int. Cl.[6] ..... A01H 5/00

[52] U.S. Cl. ..... Plt./74.1

[58] Field of Search ..... Plt./74.1

*Primary Examiner*—Howard J. Locker

*Attorney, Agent, or Firm*—Foley & Lardner

[57] ABSTRACT

A Chrysanthemum plant named Felicia particularly characterized by its flat capitulum form; daisy capitulum type; red-purple ray floret color; diameter across face of capitulum of 50 to 54 mm when fully opened; branching pattern is spreading and prolific, with 6 to 8 laterals developing after pinch when grown outside under natural daylength in fall flowerings; natural season flower date of August 8 to 16 when planting rooted cuttings on June 17 to 18 in Salinas, Calif., and of September 14 to October 1 when planting rooted cuttings June 15 to 18 in Highstown, N. J.; plant height of 23 to 28 cm when grown in fall under natural daylength with no growth regulators; and durable, uniform performance.

3 Drawing Sheets

The present invention comprises a new and distinct cultivar of Chrysanthemum, botanically known as *Dendranthema grandiflora*, and referred to by the cultivar name Felicia.

Felicia, identified as 8297 (92-543001), was originated from a cross made by Cornelis P. VandenBerg in a controlled breeding program in Salinas, Calif., in November of 1991.

The female parent of Felicia was the cultivar identified as Debonair, disclosed in U.S. Plant Pat. No. 5,324, and described as garden mum with purple flower color.

The male parent of Felicia was an unnamed seedling, identified as 8087 (92-709003), and described as a red decorative garden mum with many disc florets. The male parent was discarded from all programs on Oct. 13, 1995.

Felicia was discovered and selected as one flowering plant within the progeny of the stated cross by Cornelis P. VandenBerg in October of 1992 in a controlled environment in Salinas, Calif.

The first act of asexual reproduction of Felicia was accomplished when vegetative cuttings were taken from the initial selection in December of 1992 in a controlled environment in Salinas, Calif., by technicians working under the supervision of Cornelis P. VandenBerg.

Horticultural examination of controlled flowerings of successive plantings has shown that the unique combination of characteristics as herein disclosed for Felicia are firmly fixed and are retained through successive generations of asexual reproduction.

Felicia has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Felicia, which, in combination, distinguish this Chrysanthemum as a new and distinct cultivar:

1. Flat capitulm form.
2. Daisy capitulum type.
3. Red-purple ray floret color.
4. Diameter across face of capitulum of 50 to 54 mm when fully opened.

5. Branching pattern is spreading and prolific, with 6 to 8 laterals developing after pinch when grown outside under natural daylength in fall flowerings.
6. Natural season flower date of August 8 to 16 when planting rooted cuttings on June 17 to 18 in Salinas, Calif., and of September 14 to October 1 when planting rooted cuttings June 15 to 18 in Hightstown, N.J.
7. Plant height of 23 to 28 cm when grown in fall under natural daylength with no growth regulators.
8. Durable, uniform performance.

The accompanying photographic drawings show typical inflorescence and leaf characteristics of Felicia, with the colors being as nearly true as possible with illustrations of this type.

Sheet 1 is a color photograph of Felicia grown in natural season outside conditions in Salinas, Calif.

Sheet 2 is a black and white photograph of three views of the inflorescence of Felicia.

Sheet 3 is a black and white photograph showing the upper and under sides of the leaves of Felicia at 3 stages of development (mature, intermediate and immature). In sheets 2 and 3 a measuring tape in centimeters has been added.

Of the commercial cultivars known to the inventor, the most similar in comparison to Felicia is the cultivar identified as Empire Crown Jewel, disclosed in U.S. Plant patent application, Ser. No. 08/520,466. Reference is made to attached Chart A, which compares certain characteristics of Felicia to the same characteristics of Empire Crown Jewel.

Similar traits are capitulum form and type, flower diameter and plant height. Felicia has a slightly lighter ray floret color (RHS 70B) than Empire Crown Jewel (RHS 70A). Felicia has an earlier natural season flowering response than Empire Crown Jewel in both California and New Jersey flowerings.

In the following description color references are made to the Royal Horticultural Society Colour Chart. The color values were determined on plant material grown as a pinched garden mum grown outdoors in Salinas, Calif. on Aug. 8, 1995.

Classification:

*Botanical.*—*Dendranthema grandiflora* cv. Felicia.

*Commercial.*—Flat daisy garden mum.

INFLORESCENCE

A. Capitulum:

*Form.*—Flat.

*Type.*—Daisy.

*Diameter across face.*—50 to 54 mm when fully opened.

B. Corolla of Ray Florets:

*Color (general tonality from a distance of three meters).*—Red-purple.

*Color (upper surface).*—70B.

*Color (under surface).*—70D, streaked with 70B.

*Shape.*—Flat, straight, ray floret tip rounded.

C. Corolla of disc florets:

*Color (mature).*—15B.

*Color (immature).*—6B tinged with 151D.

D. Reproductive Organs:

*Androecium.*—Present on disc florets only; moderate pollen.

*Gynoecium.*—Present on both ray and disc florets.

PLANT

A. General appearance:

*Height.*—23 to 28 cm when grown in fall under natural daylength with no growth regulators.

*Branching pattern.*—Spreading.

B. Foliage:

*Color (upper surface).*—147A.

*Color (under surface).*—147B.

*Shape.*—Very deeply lobed, serrated.

CHART A

| CULTIVAR | Felicia | Empire Crown Jewel |
|---|---|---|
| Ray floret color | Red-purple | Red-purple |
| Capitulum form and type | Flat daisy | Flat daisy |
| Diameter across face of capitulum | 50 to 54 mm | 50 to 55 mm |
| Branching pattern | Spreading | Spreading |
| Nat. season flower date: | | |
| in Salinas, CA | Aug 8 to 16 | Aug 23 to 28 |
| in Highstown, NJ | Sep 14 to Oct 1 | Sep 25 to Oct 2 |
| Plant height: | 23 to 28 cm | 23 to 28 cm |

COMPARISONS MADE OF PLANTS GROWN UNDER NATURAL SEASON OUTDOOR CONDITIONS IN SALINAS, CALIFORNIA AND IN HIGHSTOWN, NEW JERSEY

What is claimed is:

1. A new and distinct Chrysanthemum plant named Felicia, as described and illustrated.

* * * * *

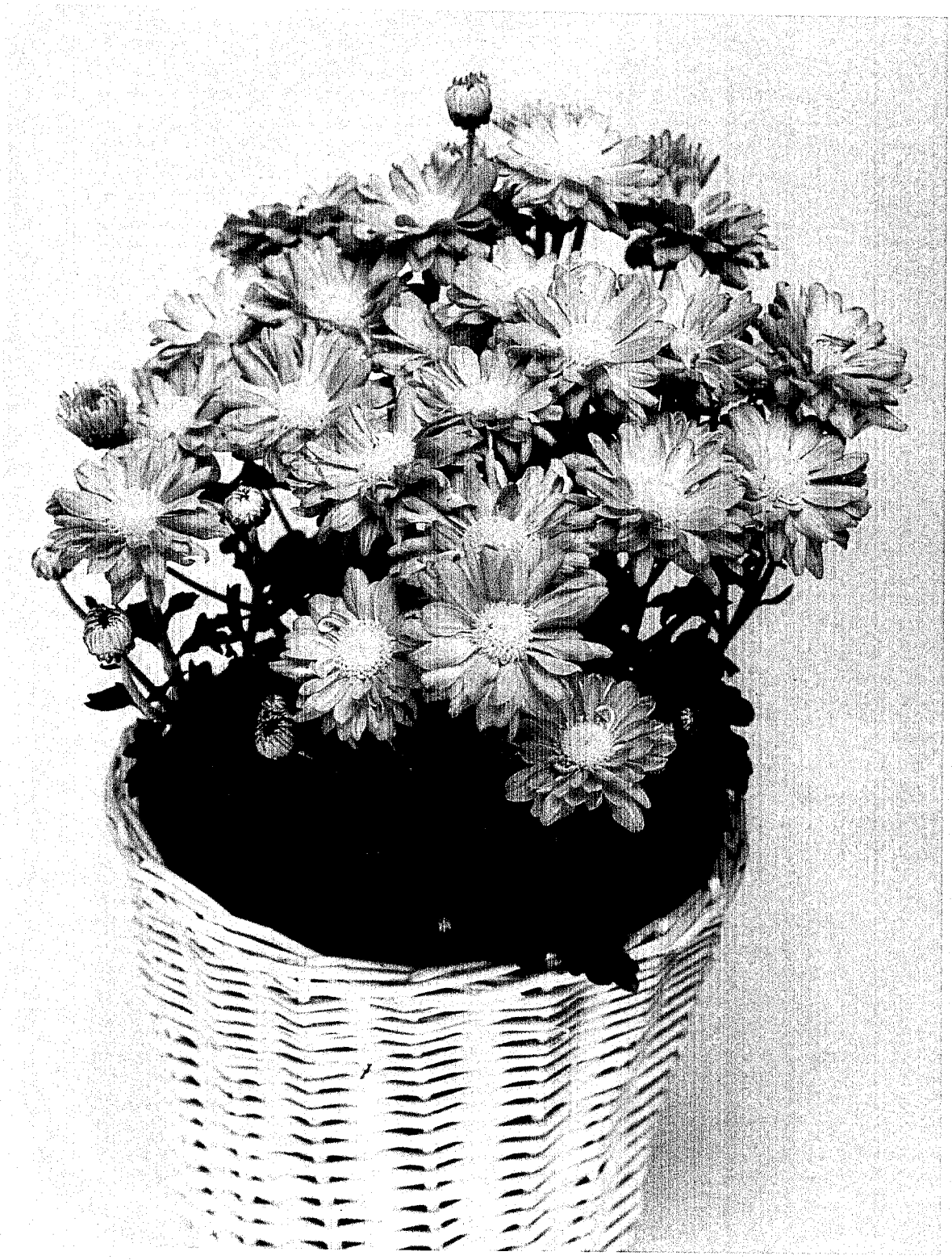

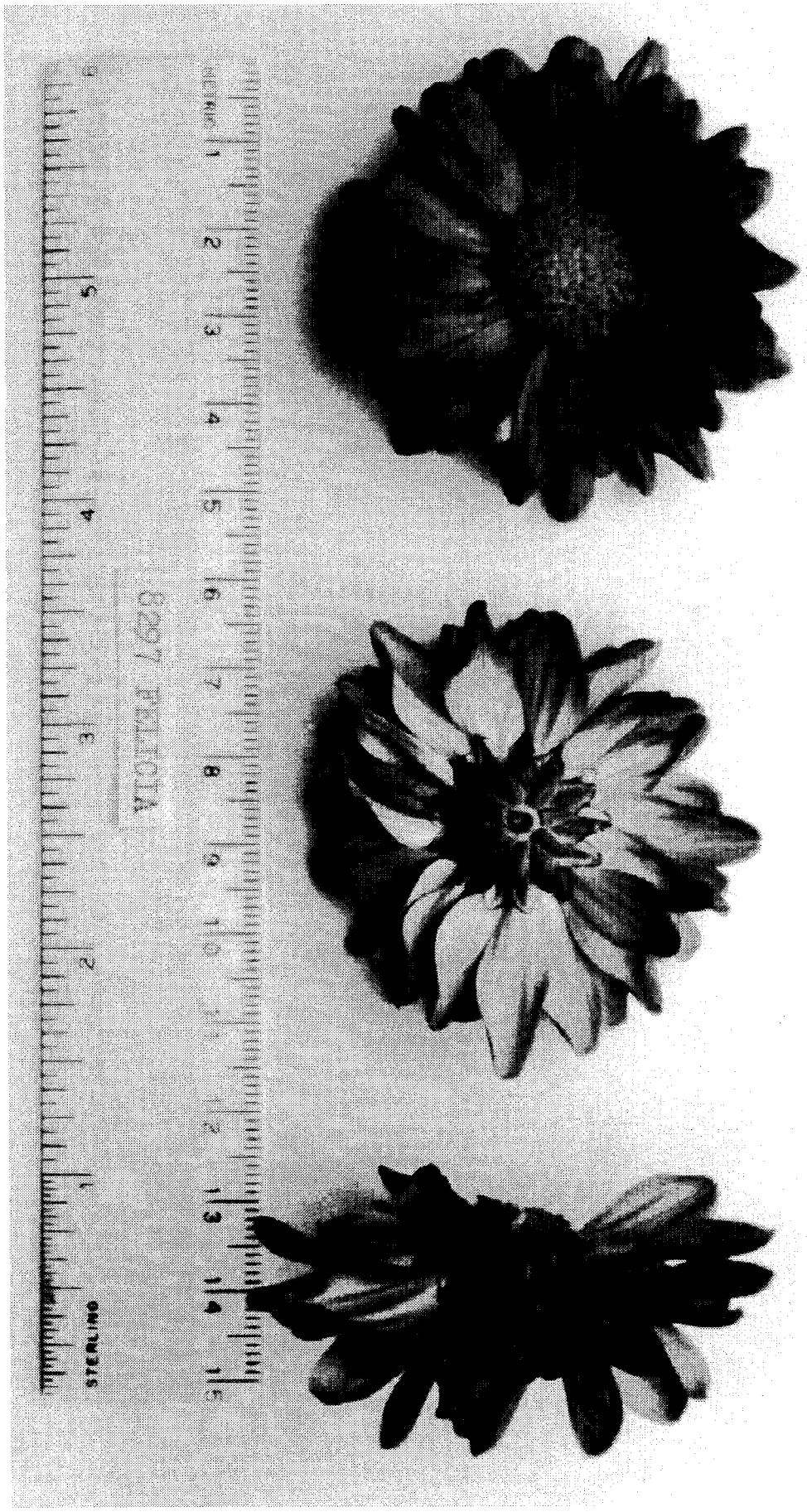
STERLING
VICTORIA 1828

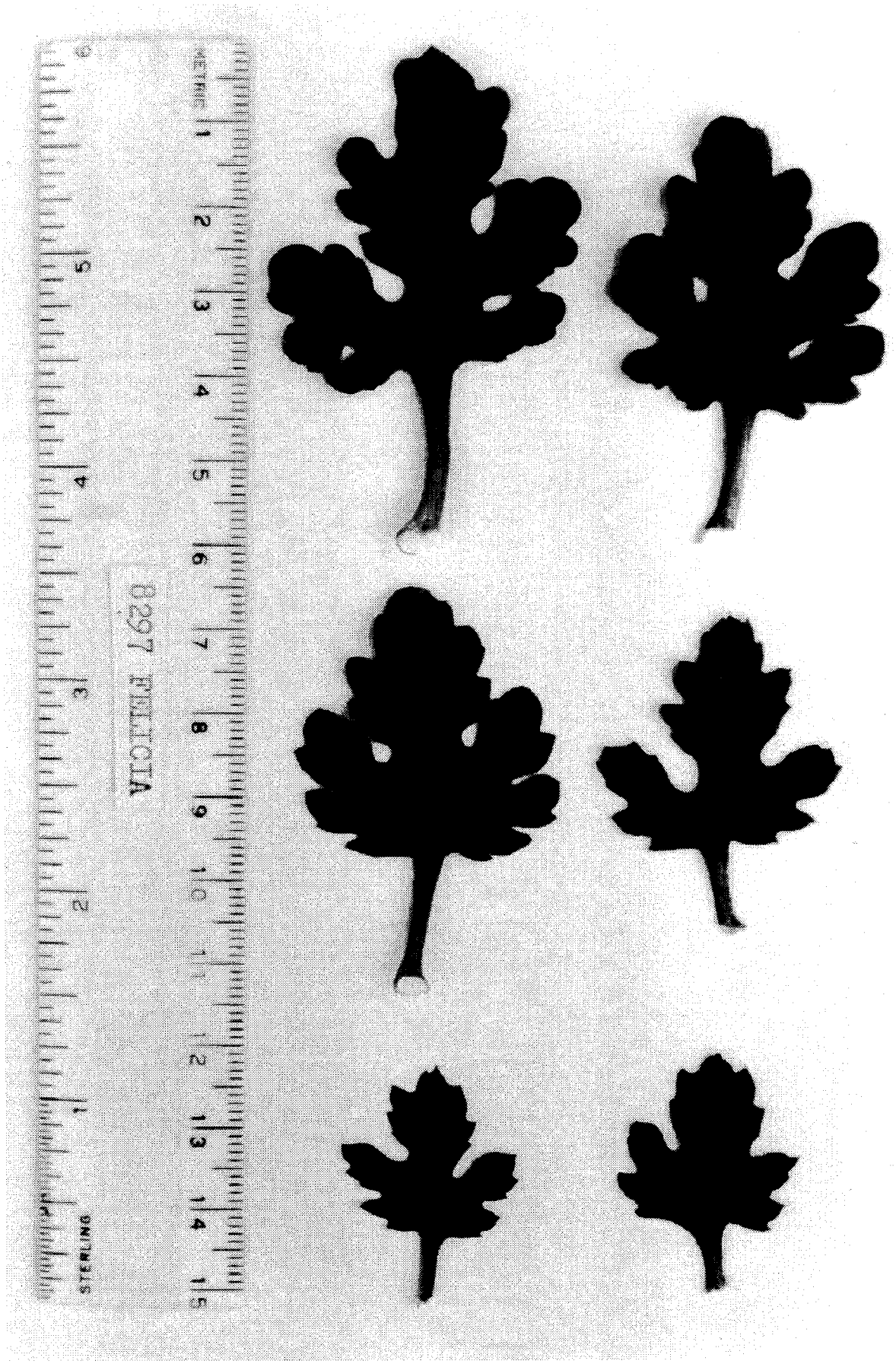
0297 FRAXINICIA
STERLING